(12) United States Patent
Lüchinger

(10) Patent No.: US 7,617,717 B2
(45) Date of Patent: Nov. 17, 2009

(54) MEASURING INSTRUMENT FOR GRAVIMETRIC MOISTURE DETERMINATION

(75) Inventor: Paul Lüchinger, Uster (CH)

(73) Assignee: Mettler-Toledo AG, Greifensee (CH)

( * ) Notice: Subject to any disclaimer, the term of this patent is extended or adjusted under 35 U.S.C. 154(b) by 272 days.

(21) Appl. No.: 11/738,197

(22) Filed: Apr. 20, 2007

(65) Prior Publication Data

US 2007/0245813 A1 Oct. 25, 2007

(30) Foreign Application Priority Data

Apr. 25, 2006 (EP) .................. 06113027

(51) Int. Cl.
*G01N 5/02* (2006.01)
(52) U.S. Cl. ............................. 73/76; 73/75
(58) Field of Classification Search ............ 73/75–76; 274/14
See application file for complete search history.

(56) References Cited

U.S. PATENT DOCUMENTS 1,593,161 A * 7/1926 Watts et al. .................... 73/75
3,994,156 A 11/1976 Koster
4,681,996 A 7/1987 Collins et al.
4,964,734 A 10/1990 Yoshida et al.
5,485,684 A 1/1996 Philipp et al.
6,255,603 B1 * 7/2001 Spannagel et al. .......... 177/180
6,521,876 B2 2/2003 Jennings et al.
2002/0063128 A1 5/2002 Revesz et al.

FOREIGN PATENT DOCUMENTS

WO 02/14848 A1 2/2002

* cited by examiner

*Primary Examiner*—Hezron Williams
*Assistant Examiner*—Rodney T Frank
(74) *Attorney, Agent, or Firm*—Standley Law Group LLP

(57) ABSTRACT

An instrument for gravimetrically determining the moisture content of a sample has a housing with a weighing device therein. The weighing device has a load-receiving portion and a sample receiver, the latter designed for connection to the load-receiving portion. The housing also contains a test compartment. When set in position to perform a measurement, the sample receiver is disposed inside the test compartment. One embodiment of a means arranged in the test compartment for heating a sample placed on the sample receiver has first and second radiation sources, with the sample receiver arranged therebetween.

22 Claims, 6 Drawing Sheets

MEASURING INSTRUMENT FOR GRAVIMETRIC MOISTURE DETERMINATION

CROSS-REFERENCE TO RELATED APPLICATIONS

This application claims a right of priority under 35 USC §119 from European patent application 06 11 3027.4, filed 25 Apr. 2006, the content of which is incorporated by reference as if fully recited herein.

TECHNICAL FIELD

The present invention relates to a measuring instrument for the gravimetric determination of moisture content.

BACKGROUND OF THE ART

To determine the moisture content in a sample, the sample is dried and the weight of the sample before and after the drying process is determined manually. Due to the extensive amount of work involved, this method is very expensive as well as error-prone.

In some cases, the weight loss can also be measured during the drying process. In a given sample, the decrease in weight is a function of the temperature, the length of the drying time, and the conditions in the test compartment, and it conforms to a weight-versus-time curve which asymptotically approaches the dry weight of the sample. The curve for the given sample is determined by comparative experiments and can be expressed mathematically through an approximation formula. A measuring instrument for gravimetric moisture determination which is appropriately equipped with available electronic technology can compute the moisture content of a sample based on the measured parameters of the aforementioned curve and based on the length of the drying time and indicate the result on a display unit. With this method, the substance to be dried no longer needs to be totally desiccated; it is sufficient to determine the coordinates of two measurement points in the weight-versus-time diagram.

As has already been mentioned at the beginning, the weight change of a sample is substantially a function of the temperature, the length of the drying time, and the conditions in the test compartment. Especially the stringent requirements imposed on the test compartment are setting a limit to the accuracy of the commercially available instruments.

The term "test compartment" in the present context means a space which is enclosed by the housing of the measuring instrument and which can be opened in order to insert or remove a sample. Also arranged inside the test compartment are a sample receiver and a means to heat the sample. The sample receiver is connected to a gravimetric measuring instrument.

Normally, the sample is spread in a thin layer onto a flat sample receiver, for example a sample tray. For a uniform heating of the sample, the sample tray is preferably positioned so that its flat area is horizontal and parallel to the planar area occupied by the sample-heating means.

As a means for heating the sample, a variety of radiation sources are used, such as heat radiators, microwave generators, halogen and quartz lamps. As was found in experiments, the type of radiation source being used and the way it is arranged in the test compartment are among the primary causes for inaccurate measurement results in existing gravimetric moisture-determination instruments.

A gravimetric moisture-determination instrument of the aforementioned type is disclosed in commonly-owned U.S. Pat. No. 5,485,684, which issued on 23 Jan. 1996 to Florian, et al. In this instrument, the sample substance is put on the weighing pan while the latter is outside of the gravimetric moisture-determination instrument. To do this, the balance is pulled out of the housing of the measuring instrument on a sliding carrier like a drawer. For a radiation source a ring-shaped halogen lamp is used which is located above the sample receiver when the instrument is in its operating condition.

One of the possibilities of preventing a thermal decomposition of the sample is to use a microwave generator as radiation source, as is disclosed in U.S. Pat. No. 6,521,876 B2, issued on 18 Feb. 2003 to Jennings, et al. One drawback of microwave heating is that samples with a non-homogeneous moisture distribution will also be non-homogeneously heated. The volatile components escaping from the heated areas of the sample, in particular moisture in the form of water vapor, can partially condense in the cold areas of the sample, so that there is a tendency for the moisture to first distribute itself within the sample before being driven out of the sample. The timing errors which occur as a result of this impose a limit on the accuracy that can be achieved in an analysis according to the calculation method described above. As an alternative to using the calculation method, one is only left with the choice to drive out all of the moisture contained in the sample. However, the smaller the amount of moisture that is present in the sample, the less heat is developed. Utensils such as weighing receptacles of a plastic material in which microwaves can generate vaporizing heat often have in themselves an inherent moisture content or an affinity for moisture, so that instead of a drying process an exchange of moisture between the sample and the weighing receptacle can take place. A locally concentrated overheating can likewise occur in weighing receptacles of a plastic material, in which case the plastic material can break down and the loss of mass due to escaping volatile decomposition products or due to substance being sublimated off the weighing receptacle can be measured erroneously as a weight loss of the sample.

For the reasons that have just been explained, it is hardly possible to determine an absolute value for the moisture content with a gravimetric moisture-determination instrument. For a more accurate determination of the moisture content of a substance, the known Karl Fischer titration method is therefore still in use. This method is very labor-intensive, prone to user errors, and expensive.

It is therefore the object to provide in a gravimetric moisture-determination instrument of the kind mentioned in the introduction having a test compartment with improved test conditions, in which the moisture content of a sample can be determined more precisely.

SUMMARY OF THE INVENTION

A gravimetric moisture-determination instrument that meets the foregoing object comprises a weighing device arranged within its housing. The weighing device comprises a load-receiving part and a sample receiver that is configured so that it can be connected to the load-receiving part. The measuring instrument further comprises within its housing a test compartment. In its measurement position, the sample receiver is set in place in the test compartment. Arranged in the test compartment is a means for heating a sample placed on the sample receiver. The heater means comprising a first radiation source and a second radiation source in an arrangement where the sample receiver is located between the first radiation source and the second radiation source. Ideally, the first radiation source is arranged above the sample receiver (in relation to the direction of the load) and the second radiation source is arranged below the sample receiver.

The term "measurement position" in the present context means that the elements arranged inside the measuring instrument are positioned in relation to each other in such a way that a measurement can be performed. In practice, this means that the sample receiver is positioned between the first radiation source and the second radiation source.

In measurement position, the sample receiver is preferably arranged so that its flat area extends in a plane that is orthogonal to the direction of the load, while the first radiation source and the second radiation source are oriented with their largest surface dimensions parallel to the sample receiver.

In principle, a single radiation source would be sufficient for a gravimetric moisture-determination instrument, since its purpose is only to drive the moisture out of the sample while affecting the sample itself as little as possible. The rate of heat generation in the test compartment should therefore not exceed a value that depends on the sample. However, the arrangement taught herein has considerable advantages over the known state of the art. By arranging two radiation sources below and above the sample receiver, one gains significantly better control over the heat distribution in the test compartment and in the sample. The sample is more uniformly heated through and in less time. The intensity of the radiation of both radiation sources can be matched appropriately to the sample and to the sample receiver that is being used. By choosing a suitable temperature profile across the thickness of the layer of the sample spread over the sample receiver, the expulsion of moisture can additionally be speeded up without causing a breakdown of the sample. In spreading the sample over the sample receiver, it is unavoidable that the layer thickness will vary from place to place. The variations depend on the sample and the method of spreading. Due to the improved control over the heat distribution in the sample, the uneven spread of the sample on the sample receiver has less influence on the result of the measurement.

The term "sample receiver" in this context essentially means the load receiver or the weighing pan of a gravimetric measuring instrument.

Ideally, the weighing device and the test compartment are arranged side-by-side in the housing of the measuring instrument. At least one wall of the test compartment, preferably a wall that faces towards the weighing device, has at least one passage opening through which a connecting member reaches which connects the weighing device to the sample receiver that is arranged in the test compartment.

In a preferred embodiment, the respective emission levels of the first and second radiation source can be controlled and/or regulated independently of each other. Ideally, the measuring instrument is equipped with electronic control and/or regulation so that a diversity of measurement programs with defined temperature-versus-time profiles can be prescribed and the collected measurement values can in some cases also be analyzed directly.

To realize the last-named concept, the temperature in the test compartment is measured through suitable means, for example a temperature sensor that is arranged in the test compartment. To obtain a more accurate representation of the test conditions, there can additionally be a humidity sensor arranged in the test compartment.

The radiation source can be selected from a multitude of possibilities. For the heating of the sample one can use for example a heating plate, a heating foil, a heat radiator, a heat coil, a diversity of broad-band radiation sources such as a halogen heat lamp or a quartz heat lamp, a monochromatic light source, a Peltier element, or a microwave generator.

A combination of different radiation sources offers particularly interesting possibilities, where the respective radiation systems employed in the first radiation source and the second radiation source are different from each other. For example, combining a microwave generator with a heating plate can prove to be particularly advantageous, depending on the sample to be tested.

In order to provide the measuring instrument with the broadest possible flexibility, at least one of the radiation sources should have a plug-in connector which couples the radiation source mechanically to the housing and/or electrically to an energy source. This is advantageous for two reasons. First, it makes exchanging a radiation source significantly easier. Second, it offers the possibility that different types of radiation sources can be put together in a set of modules, so that the user of the measuring instrument can select from this set a combination of radiation sources that is ideal for the tests to be performed.

To allow the gases and/or vapors that are driven out of the sample to be removed evenly from above the sample, the radiation source ideally has passage openings through which the volatile substances and/or vapors can escape.

To simplify placing the sample in the test compartment and subsequently removing it, the sample receiver can be configured so that it can be coupled to and uncoupled from the load-receiving part.

The overall architecture of the measuring instrument can be embodied in different configurations. In a first embodiment of the measuring instrument, the first radiation source and the second radiation source are mechanically connected to each other as a unit, wherein this unit is supported by a movable part of the housing with the freedom to swivel about a substantially vertical axis. Depending on its configuration, when this unit is swiveled out, the sample receiver can be freely accessible.

In a second embodiment of the measuring instrument, the first radiation source is supported by and connected to a movable housing part that is configured as a lid, wherein the lid is hinged to a fixed part of the housing so that it can pivot about a substantially horizontal hinge axis. The second radiation source is rigidly connected to the fixed part of the housing. In the raised position of the lid, the sample receiver can be freely accessible.

In a third embodiment of the measuring instrument, the first and the second radiation source are rigidly connected to the fixed part of the housing and the weighing device together with the sample receiver is configured so that it can slide out of the housing, supported by a movable housing part that is constrained to a linear range of displacement. Depending on the design of the weighing device, the sample receiver can be freely accessible when the weighing device is slid out of the housing.

In a fourth embodiment of the measuring instrument, the first and the second radiation source are rigidly connected to the fixed part of the housing, and the weighing device together with the sample receiver is constrained to allow swiveling about a substantially vertical axis. Depending on the configuration of the weighing device, the sample receiver can be freely accessible in the swiveled-out position of the weighing device.

In a fifth embodiment of the measuring instrument, the weighing device with the sample receiver is rigidly connected to the housing, and at least the first radiation source is arranged on a housing part that is capable of a substantially horizontal movement. In the measuring position, this radiation source is located above the sample receiver. In the sample-loading position, the sample receiver is no longer covered up by the radiation source, but is freely accessible. Of course, it is also possible to arrange the first as well as the second radiation source in the movable housing part, so that in the sample-loading position neither of the radiation sources is located below or above the sample receiver.

In a preferred embodiment, a suction device is arranged adjacent to the test compartment, preferably above the first radiation source. Its purpose is to remove the volatile substances and/or vapors. The suction device slightly lowers the pressure level in the test compartment, whereby a gaseous medium is pulled in from outside the measuring instruments, for example through passages in the walls of the test compartment. The gaseous medium is channeled in an appropriate manner through the test compartment where it can absorb the volatile substances and/or vapors escaping from the sample, whereupon it is removed from the test compartment through the suction device. Of course, the gaseous medium can also be fed through the test compartment under an overpressure.

The suction device is not limited to active systems such as for example an exhaust passage with a ventilator or a vacuum pump. If a gas delivery device introduces a gaseous medium under an overpressure from the outside into the test compartment, the gas delivery device and the exhaust opening for the removal of the gases from the test compartment likewise constitute a suction device.

The weighing results of the weighing device can be strongly influenced by the radiation sources. To provide thermal insulation, the wall of the test compartment is preferably configured as a double wall at least between the test compartment and the weighing device, and the gaseous medium aspirated from outside the measuring instrument, preferably air, is directed to flow inside the double wall. The gaseous medium can, of course, also be introduced into the measuring instrument under overpressure. In the test compartment or inside the double wall there can in addition be a means to eliminate electrostatic charges of the sample, for example an ionizer, in order to eliminate electrostatic charges in the test compartment.

With preference, the gaseous medium is chemically stable and has a strong inertia against reacting with the sample and the materials of the test compartment. Gaseous media with these qualifications include for example protective gases such as nitrogen and noble gases such as argon.

In special cases, it is also possible to use a gaseous medium that reacts with the escaping vaporous or gaseous substances in order to counteract a re-absorption of the substances by the sample. In the case of water vapor, one can use for example a variety of halogens.

It is of advantage for special applications, if the gaseous medium has a predefined moisture content. This helps to improve the reproducibility of comparison measurements.

The weighing result is affected by currents moving through the test compartment, whether they are actively generated by means of a suction device or caused by purely thermal effects. The gaseous medium which rises from bottom to top in the test compartment pushes against the underside of the sample receiver and thereby lowers the measured weight of the sample. The lifting force on the sample due to buoyancy on the other hand decreases with rising temperature. Effects of this kind can be compensated electronically by determining a compensation value with a dummy sample prior to the actual measurement.

Preferably, the measuring instrument is equipped with a calibration device which serves to calibrate the weighing device either on demand or automatically.

The calibration device can include one calibration weight or a plurality of calibration weights. In a particularly preferred embodiment, the center of mass of the one or more calibration weights during a calibration process lies on an axis that is oriented in the direction of the load and passes through the center of gravity of the sample receiver and/or of the sample. The purpose of this is to avoid eccentric load errors (also referred to as corner load errors) in the correction factor that is determined in the calibration process.

The afore-described embodiments of the measuring instrument allow a multitude of diverse processes to be carried out. One such process, which serves to determine the moisture content of a sample by measuring the weight loss over a predetermined test duration with a specified temperature profile, includes substantially the following steps:

conditioning of the test compartment to a prescribed temperature by means of at least one of the radiation sources, opening the test compartment, placing the sample in the test compartment, and closing the test compartment, determining the sample weight in predetermined time intervals, for example at the start of the test and at the end of the test, and/or continuously determining the weight loss over the entire duration of the test, and removing the sample, evaluating the measurement result and/or transmitting the measurement result to an indicating unit.

By conditioning the test compartment before starting the actual measurement, it is possible to achieve stationary conditions in the test compartment, which has a very positive effect on the reproducibility of the measurement results. The reproducibility of results is an important property of a gravimetric moisture-determination instrument. It is an absolute prerequisite to allow comparisons between results. In random-sample tests of process materials such as for example a polymer granulate, the measurement results are compared to empirical reference values. The measurement results and the comparison values are used to determine the pretreatment of the materials and/or the setting data for the processing machines.

A further procedure can be performed with the measuring instrument if it is equipped with a system for conditioning the gaseous medium. This procedure serves to determine the affinity of the sample to moisture by measuring the weight gain over a predetermined test duration and under a prescribed temperature profile. This allows for example to simulate the storage of process materials. The data obtained from the procedure allow a stepwise or continuous adaptation of the processing machines to the changing condition of the materials. The method for determining the affinity to moisture substantially includes the following steps:

opening the test compartment, placing the sample in the test compartment, and closing the test compartment, conditioning the sample to a predetermined moisture content, setting the test compartment to a predetermined temperature by means of at least one of the radiation sources, injecting a gaseous medium into the test compartment with a known moisture content, at a predefined volume flow rate and a predefined temperature profile at least over the duration of the test period, determining the sample weight at the start and end of the test and/or continuously determining the weight gain over the entire duration of the test, and removing the sample, evaluating the measurement result and/or transmitting the measurement to an indicator unit.

Each of the foregoing processes involved conditioning of the test compartment. A compensation of the errors due to buoyancy and draft currents of the gaseous medium can also be performed during this conditioning phase if desired.

The method for the electronic correction of an error due to buoyancy effects or draft currents in the collected measurement results includes substantially the following steps:

placing a reference object into the test compartment, for example a empty sample tray of the type used to hold the sample, determining the base weight value for the reference object, determining the correction weight values for the reference object in predetermined measurement intervals and/or continuously measuring the weight change over the entire test duration, calculating the correction values or the correction profile over the entire test duration by subtracting the base weight value from the correction weight values, storing the correction values or the correction profile in a memory module, removing the reference object from the test compartment, and performing the measurements on the sample, taking into account the correction values determined by the first five steps.

All of the values are determined by means of the weighing cell. The memory module is part of an electronic module, wherein the electronic module can be configured as a single module or in the form of several mutually connected modules. The electronic module takes on a variety of tasks such as for example:

a. receiving and processing of measurement values of the weighing device, b. storing of input data of the user, for example data that are specific to the sample, c. regulation and control of the radiation sources, d. regulation and control of the suction device, if applicable, e. compensation of influence factors from the ambient environment on the measuring instrument, f. evaluation and memory storage of the measurement results, g. transmitting the measurement results to an indicator unit, h. management of the data, i. execution of programs and test procedures that are stored in a memory unit.

BRIEF DESCRIPTION OF THE DRAWINGS

Details of the measuring instrument are presented in the description of the embodiments illustrated in the drawings, wherein.

DETAILED DESCRIPTION OF THE PREFERRED EMBODIMENTS

Figure 1:
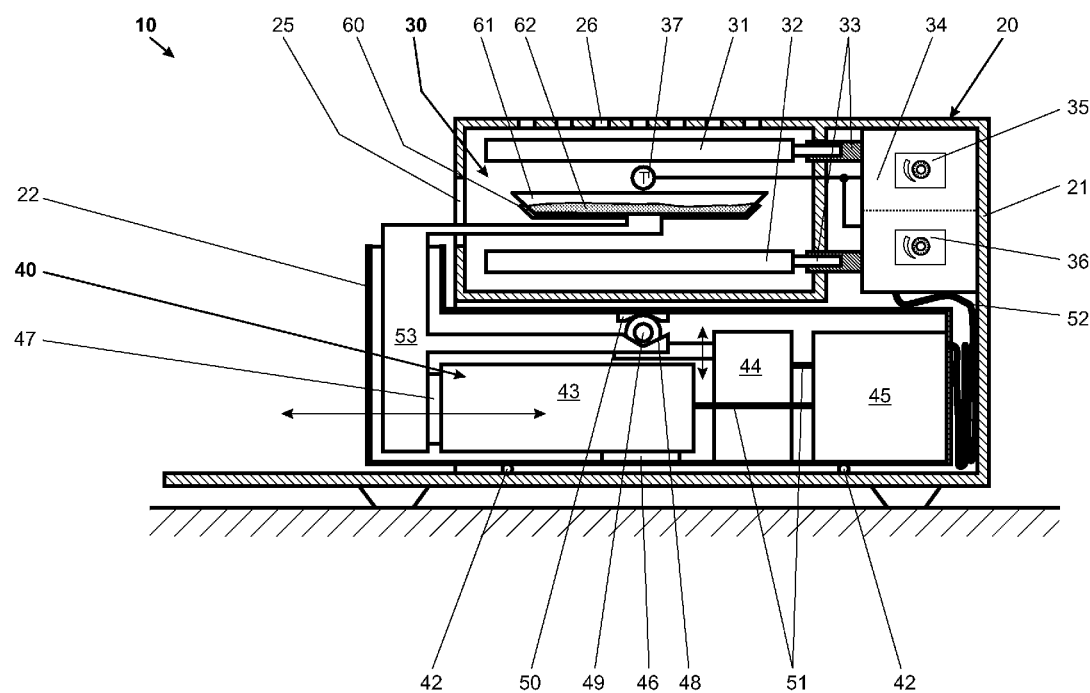
FIG. 1 is a cross-sectional view of a first embodiment of a measuring instrument, with a weighing device in place for performing the measurement.

FIG. 1, in a sectional view, illustrates a measuring instrument 10 in a first embodiment. The measuring instrument 10 has a housing 20 in which a test compartment 30 is arranged. The housing 20 is divided into a movable housing part 22 and a stationary housing part 21. Arranged below the test compartment 30 is a weighing device 40 on the movable housing part 22 which is constrained to a substantially horizontal mode of displacement. The movable housing part 22 glides on rollers 42 (shown only schematically) in the stationary housing 21. Of course, it is also possible to use commercially available drawer guides such as dual pull-out tracks and the like. The movable housing part 22 which is configured as a hollow shell contains a weighing cell 43, a calibration-weight-loading mechanism 44 and at least one electronic module 45 which are connected to each other through communicating means 51. The electronic module 45 contains at least one signal-processing module (not shown in detail here) and in some cases also a control and/or regulation module. The weighing cell 43 has at least one stationary portion 46 and a load-receiving portion 47. Known types of weighing cells are for example elastically deforming bodies carrying strain gauges, or weighing cells based on the principle of electromagnetic force compensation, or weighing cells with oscillating strings, capacitive weighing sensors and the like. The stationary portion 46 is rigidly connected to the movable housing part 22. Arranged on the load-receiving portion 47 is a connecting member 53 which connects a sample receiver 60 to the load-receiving portion 47. As illustrated, a sample tray 61 with a sample 62 can be set on the sample receiver 60. With a suitable design of the sample receiver 60, one could of course also put the sample 62 directly on the sample receiver 60.

Further, a calibration weight receiver seat 48 is formed on the connecting member 53. A calibration weight 49 can be put on the weight receiver seat 48 by means of the calibration weight handling mechanism 44 actuated either by the user or under the control of the measuring instrument 10, in order to determine a correction value for the measuring signal based on the current operating condition of the measuring instrument 10. After the correction value has been determined, the calibration weight 49 is disconnected again from the calibration weight receiver seat 48 and held by the calibration weight handling mechanism 44 against a resting cradle 50 until the next calibration cycle takes place. Ideally, as a way to avoid eccentric load errors in the correction value, the mass center of the calibration weight 49 or—if applicable—the combined mass center of a plurality of calibration weights 49—lies close to an axis that passes through the center of gravity of the sample receiver 60 and/or of the sample tray 61 and/or the sample 62. The term "eccentric load error" (also referred to as corner load error) means the deviation that occurs in the weight measured by a weighing device for one and the same load when the latter is placed eccentrically on the sample receiver 60 in comparison to when it is put in a centered position.

The weighing device 40 as illustrated in FIG. 1 is in its measuring position, which means that the sample receiver 60 with the sample tray 61 set in place is inside the test compartment 30. A first radiation source 31 is arranged in the test compartment 30 substantially parallel to the flat area of the sample tray 60 in order to achieve as much as possible a homogeneous heat distribution at least on the surface of the sample 62. A second radiation source 32, which irradiates the sample from the underside, is arranged in the test compartment 30 below the sample receiver 60 and substantially parallel to the latter. However, it is not an absolute requirement for the radiation sources 31, 32 to be arranged so that their two largest planar dimensions are parallel to the sample receiver 60. Depending on the sample 62 and on the measurement to be performed, it can also be advantageous to use a first radiation source 31 and/or a second radiation source 32 that is set at an oblique angle to the sample receiver 60. With the double-sided irradiation from below and from above one achieves a more homogeneous heat distribution in the sample 62. As a result, in comparison to a sample 62 that is irradiated only from one side, the bilaterally irradiated sample 62 will have fewer locally concentrated temperature peaks which could cause a thermal breakdown of the sample substance in these hot spots. If the sample 62, for example a polymer substance, has a relatively low melting point, the surface of the sample 62 can melt locally under non-homogeneous heating and impede the escape of moisture from the sample 62. This can lead to massive errors in the calculated end result in cases where a computing method is used that involves time-dependent parameters.

To allow the moisture given off by the sample 62 to escape from the test compartment 30, there are vent openings 26 arranged at appropriate places in the housing 20, preferably above the first radiation source 31. In order to achieve a sufficient amount of circulation within the test compartment 30, air inlet openings need to be provided at an appropriate location, preferably below the second radiation source 32. As a practical solution, the sample-loading opening 25 simultaneously serves for the ventilation of the test compartment 30, so that no additional ventilation openings are needed, as shown in FIG. 1.

Ideally, the radiation sources 31, 32 are connected mechanically to the housing 20 and electrically to a voltage source 34 by way of releasable plug-in connections 33. This allows the radiation sources 31, 32 to be uninstalled from the test compartment 30 for cleaning or repair without a major effort. Furthermore, with the use of plug-in connections 33, the user of the measuring instrument 10 is able to combine different radiation sources 31, 32 with each other which have different ways of functioning. This allows the user to create conditions in the test compartment which are matched to the sample 62. The voltage source 34 in FIG. 1 is equipped with a first control-/regulating device 35 which serves to influence the radiation output of the first radiation source 31 and a second control-/regulating device 36 which serves to influence the radiation output of the second radiation source 32. A schematically illustrated temperature sensor 37 measures the temperature of the sample 62 and provides the first and second control-/regulating device 35, 36 with the data required for the regulation the radiation sources 31, 32. The voltage source is further connected through at least one flexible connection 52 to the weighing device 40, more specifically to the electronic module 45. This allows the control-/regulating devices 35, 36 to receive directions from the electronic module 45.

Figure 2:
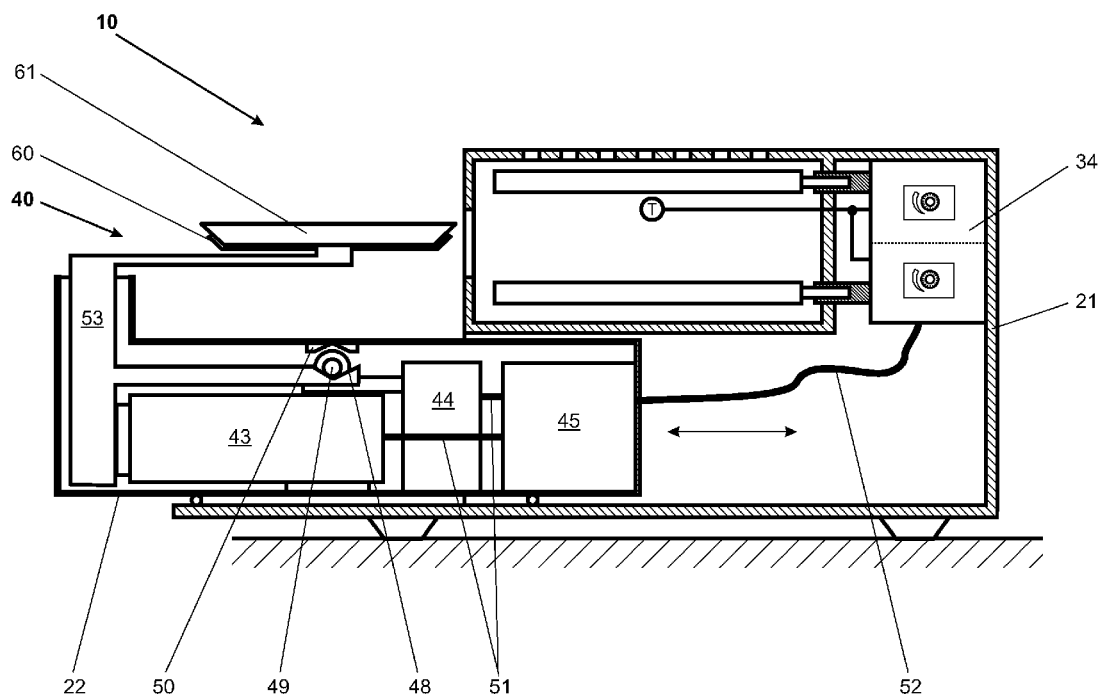
FIG. 2 is a cross-sectional view of the FIG. 1 measuring instrument, with the weighing device slid out of the measuring instrument.

FIG. 2 shows the FIG. 1 measuring instrument 10 with the weighing device 40 slid out of the stationary housing part 21. The weighing device 40 substantially comprises the movable housing part 22, the weighing cell 43, the connecting member 53, the sample receiver 60, the calibration weight handling mechanism 44, the calibration weight 49, the resting cradle 50, the electronic module 45, as well as the communicating means 51. As can be seen in FIG. 2, the connection 52 between the voltage source 34 and the electronic module 45 needs to be flexible, so that the weighing device 40 can be pulled out of the stationary housing part 21 in order to facilitate placing a sample tray 61 and/or a sample on the sample receiver 60 as well as removing the sample tray 61 and/or the sample. In FIG. 2, the calibration weight 49 has been set down on the calibration weight receiver seat 48, which means that a correction value is being determined by the electronic module 45 of the weighing device 40.

Figure 3:
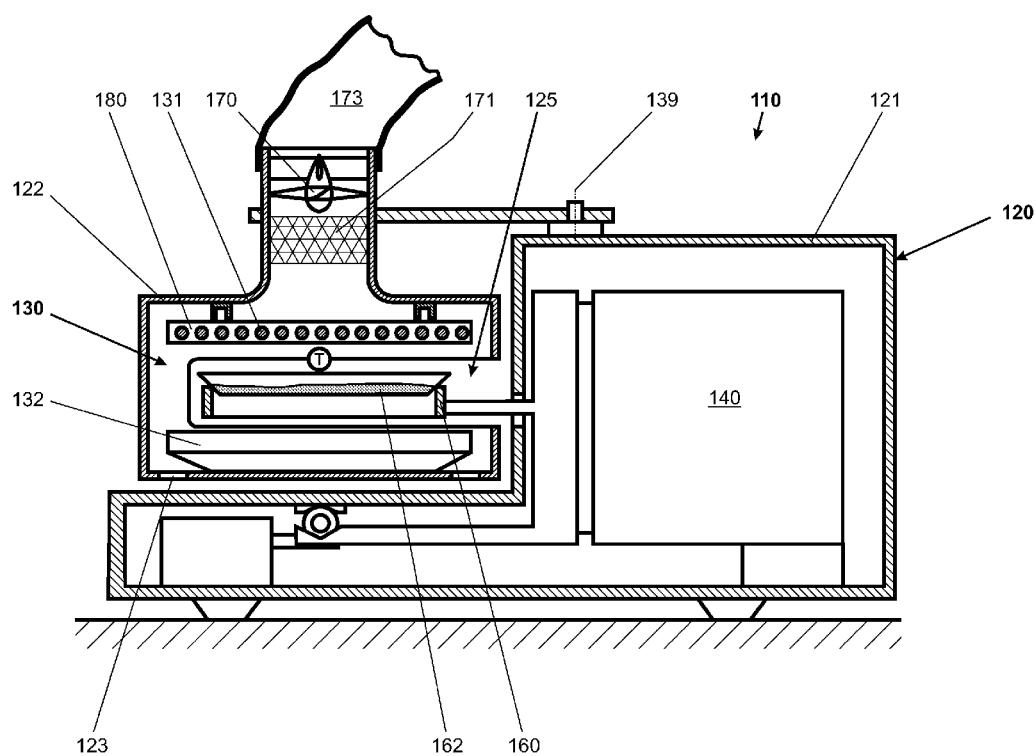
FIG. 3 is a cross-sectional view of a second embodiment of the measuring instrument.

FIG. 3 represents a cross-sectional view of a second embodiment measuring instrument 110. A weighing device 140 arranged in the housing 120 has substantially the same elements as were named above in the description of FIG. 1 for the weighing device 40. The housing 120 is divided into a stationary housing part 121 and a movable housing part 122.

Unlike the arrangement of FIG. 1, the weighing device 140 is not arranged in a horizontally movable housing part but in the fixed housing part 121. The weighing device 140 is largely enclosed by the stationary housing part 121. Only a sample receiver 160 which is connected to the weighing device 140 protrudes from the stationary housing part 121 and reaches into the space of the movable housing part 122 when the latter is set in position for performing measurements. Receptacles of different shapes such as sample trays 162, crucibles and the like can be places on this sample receiver 160 which is ring-shaped.

The movable housing part 122 forms the outer envelope of a unit which is pivotally connected to the stationary housing 121 so as to allow the movable housing part 122 to swivel about a vertical pivot axis 139. A test compartment 130 is formed in the interior of the movable housing part 122, with a first radiation source 131 arranged in the upper part of the test compartment 130 and a second radiation source 132 arranged in the lower part of the test compartment 130. The movable housing part 122 further has a sample-loading opening 125 which is configured in such a way that the sample receiver 160 with the sample 162 in place does not touch the movable housing part 122 when the unit is swiveled. As shown in FIG. 3, in the measuring position of the apparatus the test compartment 130 encloses the sample receiver 160, with the first radiation source 131 arranged above the sample receiver 160 and the second radiation source 132 arranged below the sample receiver 160.

The first radiation source 131 is interrupted by a plurality of breakthrough openings 180 so as to form a grate, which allows the vapors and/or volatile substance to be removed more easily from the vicinity of the sample 162 through the openings 180. A suction device 170 is built into the movable housing part 121 above the first radiation source 131. The suction device 170 lowers the pressure in the test compartment 130, so that for example the ambient air surrounding the measuring instrument 110 is drawn into the test compartment 130 through vent openings 123 of the movable housing part 121. The air taken in is heated in the test compartment 130 by the radiation sources 131, 132, absorbs the moisture escaping from the sample 162, and leaves the test compartment 130 by way of the suction device 170. The flow rate of the aspirated gaseous medium which absorbs the moisture driven out of the sample 162 can be controlled by way of the suction power of the suction device 170. To deal with volatile substances which have for example a strong odor of their own, which are toxic or caustic, the suction channel of the suction device 170 can additionally be equipped with a filter 171, as shown in FIG. 3, for example a woven mesh insert, an adsorption filter and/or a condenser. Depending on the existing infrastructure, it is possible to send the gaseous medium with the absorbed moisture for example into a duct of a ventilation system of the building through a hose 173 that is connected to the suction system 170.

Figure 4:
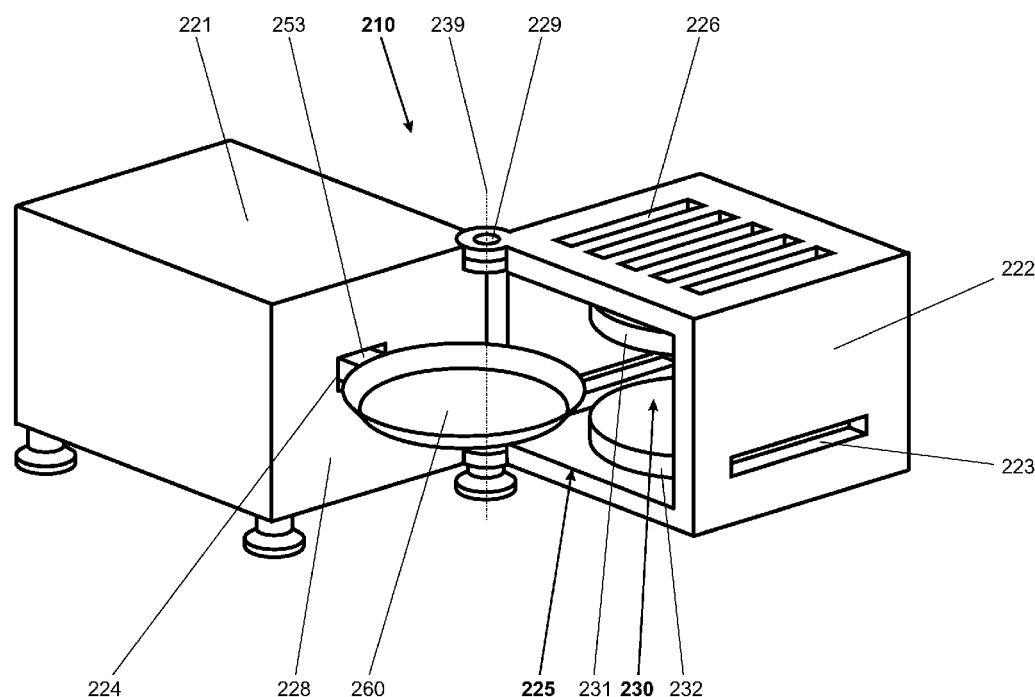
FIG. 4 is a perspective view of a third embodiment of the measuring instrument, in the opened condition.

FIG. 4 shows a three-dimensional drawing of a third embodiment measuring instrument 210 in the opened condition. This third embodiment represents a variant of the measuring instrument 110 presented in FIG. 3. The weighing device is arranged inside a stationary housing part 221 and is hidden inside the latter. At least one wall 228 of the stationary housing part 221 has a passage 224 through which a connecting member of the weighing device reaches to the outside. The connecting member 253 has a sample receiver 260 rigidly connected to it, which is configured as a weighing pan in FIG. 4 and is shown without a sample placed on it.

On one edge portion of the wall 228, a hinge 229 is formed which connects a movable housing part 222 to the stationary housing part 221. The hinge 229 has a vertical pivot axis 239 which is arranged parallel to the direction of the load. The hinge 229 which connects the housing parts 222 and 221 to each other does not necessarily have to be arranged in the place shown in FIG. 4. It can be arranged at the opposite edge of the wall 228, but also along the upper edge portion of the wall 228, in which case the pivot axis 239 is aligned horizontally.

The movable housing part 222 has a sample-loading opening 225 which in the measuring position of the measuring instrument 210 is closed off by the wall 228. Thus, the walls of the movable housing part 222 and the wall 228 of the stationary part together form a test compartment 230 which is shown in FIG. 4 in the open condition where it allows free access to the sample receiver 260. A first radiation source 231 and a second radiation source 232 are arranged in such a way in the movable housing part 222 that, in the measuring position of the instrument 210, the first radiation source 231 is arranged above and the second radiation source 232 below the sample receiver 260. The movable housing part 222 further has air inlet openings 223 in the sidewalls and outlet openings 226 above the first radiation source 231.

Figure 5:
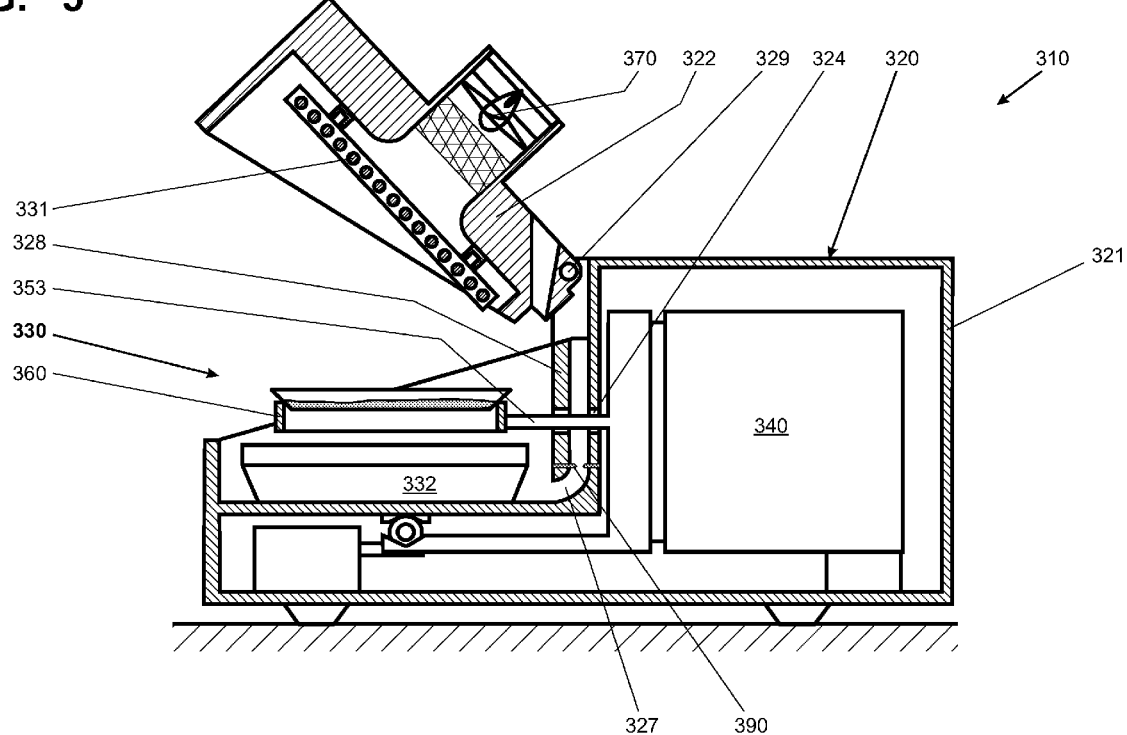
FIG. 5 is a cross-sectional view of a fourth embodiment of the measuring instrument.

FIG. 5 shows a sectional view of the measuring instrument 310 in a fourth embodiment. A weighing device 340 which is arranged in the housing 320 has substantially the same elements as were described above for the weighing device 40 of FIG. 1. The housing 320 is divided into a stationary housing part 321 and a movable housing part 322. The movable housing part 322 is configured as a lid in which a first radiation source 331 is arranged. As described in the context of FIG. 3, there is a suction device 370 incorporated in the movable housing part 322 above the first radiation source 331. This movable housing part 322 is connected to the stationary housing part 321 through a hinge 329 in the upper portion of the housing 320, with the pivot axis of the hinge 329 being substantially horizontal. The movable housing part 322 forms the upper part of a test compartment 330.

The lower part of the test compartment 330 is formed in the stationary housing part 321. Arranged in the latter is a second radiation source 332. The connecting member 353 which is mechanically connected to the weighing device 340 is likewise reaching into the lower part of the test compartment 330 in such a way that a sample receiver 360 which is connected to the connecting member 353 occupies a position above the second radiation source 332. To provide thermal insulation, a wall 328 of the stationary housing part 321 is configured at least partially as a double wall between the weighing device 340 and the test compartment 330. As illustrated in FIG. 5, the double-walled arrangement forms a ventilation channel 327 through which a gaseous medium can be directed into the test compartment 330. The medium flowing during the measuring process cools the wall 328, so that the heat radiated from the test compartment 330 cannot penetrate into the housing part that contains the weighing device 340.

There can further be various auxiliary device arranged in the ventilation channel 327. For example, the gaseous medium can be ionized by means of an ionizer 390 in order to eliminate electrostatic charges. As in the preceding examples, the wall 328 likewise has a passage opening 324. The opening 324 can be configured as an enclosed passage, so that none of the medium flowing through the ventilation channel 327 can enter through the passage opening 324 into the into the test compartment 330.

Figure 6:
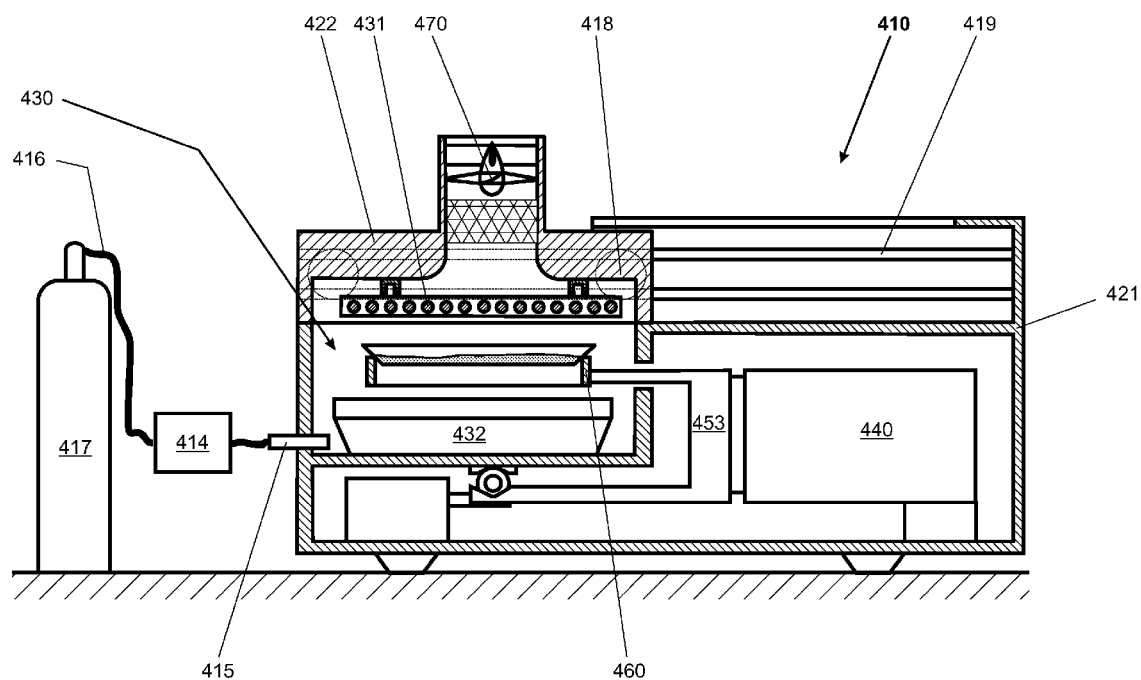
FIG. 6 is a cross-sectional view of a fifth embodiment of the measuring instrument.

FIG. 6 shows a sectional view of the measuring instrument 410 in a fifth embodiment. The stationary housing part 421 and the elements arranged inside it, such as a weighing device 440, a sample receiver 460, a connecting member 453, as well as a second radiation source 432, are substantially analogous to the elements which have been discussed above in the description of FIG. 5. The movable housing part 422 with the elements arranged in it, such as a first radiation source 431 and a suction device 470, are substantially analogous to the elements which have been discussed above in the description of FIG. 5. However, unlike the arrangement in FIG. 5, the movable housing part 422 is not connected by a hinge to the stationary housing part 421 but is guided by means of rollers 418 and guide tracks 419 that allow linear movement of the movable housing part 422 in the stationary housing part 421. Instead of the ventilation channel 327, the test compartment 430 has a gas inlet port 415 which is connected by a flexible house 416 to a pressurized container 417 or to a conduit system installed in the building. The pressurized container 417 stores a gaseous medium which is preferably conditioned by beans of a conditioning device 414, so that when it enters the test compartment 430, the gaseous medium has a defined and constant moisture content. Since the gaseous medium flows into the test compartment 430 at an above-atmospheric pressure, the suction device 470 can also be replaced by outlet openings.

The embodiments presented herein illustrate measuring instruments with different properties and features for the gravimetric determination of moisture content. For the sake of clarity, the different properties and features have been shown in different embodiments, but it is also possible to realize only one, or some, or all of the proposed features and properties in one measuring instrument.

What is claimed is:

1. A gravimetric measuring instrument for a sample, comprising:
   a housing;
   a test compartment arranged inside the housing;
   a weighing device installed in the housing, the weighing device comprising:
      a load-receiving portion; and
      a sample receiver, with a flat-area dimension that is substantially orthogonal to a direction of the load when connected to the load-receiving portion and disposed inside the test compartment when positioned to perform a measurement; and
   first and second radiation sources, arranged in the test compartment respectively above and below the sample receiver, a flat-area dimension of each radiation source being parallel to the sample receiver flat-area dimension.

2. The measuring instrument of claim 1, wherein:
   the weighing device and the test compartment are arranged side-by-side in the housing, a wall of the test compartment has a passage opening therethrough, and a connecting member that connects the sample receiver to the load-receiving portion extends through the passage opening.

3. The measuring instrument of claim 1, further comprising:

a means for electronically controlling and/or regulating an emission level of the respective radiation sources, the control and/or regulation being achieved independently for each radiation source.

4. The measuring instrument of claim 1, wherein:

the respective radiation sources are each selected from the group consisting of: a heating plate, a heating foil, a broad-band light source, a monochromatic light source, a heat radiator, a heat coil, a Peltier element, and a microwave generator.

5. The measuring instrument of claim 4, wherein:

at least one of the radiation sources is provided with openings that allow the passage of volatile substances, gases and/or vapors.

6. The measuring instrument of claim 4, wherein:

at least one of the radiation sources comprises a plug-in connector for releasably connecting the radiation source mechanically to the housing and/or electrically to a voltage source.

7. The measuring instrument of claim 1, wherein:

the sample receiver is configured to be both coupled to and uncoupled from the load-receiving portion.

8. The measuring instrument of claim 1, wherein:

the respective radiation sources are mechanically connected to each other as a unit, and a movable part of the housing supports the radiation source unit in a manner that allows the radiation source unit to swivel about a substantially vertical axis, to facilitate access to the sample receiver.

9. The measuring instrument of claim 1, wherein:

a movable part of the housing is connected to and supports the first radiation source, the movable housing part being configured as a lid that is hingedly attached to a stationary part of the housing, allowing the movable housing part to pivot about a substantially horizontal hinge axis to facilitate access to the sample receiver, and wherein the second radiation source is rigidly connected to the stationary housing part.

10. The measuring instrument of claim 1, wherein:

a stationary part of the housing is rigidly connected to each of the radiation sources, and a movable part of the housing has both the sample receiver and the weighing device arranged with it, the movable housing part being guided for linear movement to slide out of the stationary housing part to facilitate access to the sample receiver.

11. The measuring instrument of the claim 1, wherein:

a stationary part of the housing is rigidly connected to the weighing device; and a movable part of the housing has at least one of the radiation sources arranged thereon, the movable housing part adapted for substantially horizontal displacement to facilitate access to the sample receiver.

12. The measuring instrument of claim 1, further comprising:

a suction device, arranged adjacent to the test compartment.

13. The measuring instrument of claim 12, wherein:

the suction device is positioned above the first radiation source.

14. The measuring instrument of claim 2, wherein:

the test compartment wall is a double wall, at least between the test compartment and the weighing device, and a gaseous medium is directed to flow inside the double wall between the test compartment and the weighing device.

15. The measuring instrument of claim 14, wherein:

the gaseous medium is air.

16. The measuring instrument of claim 14, wherein:

the gaseous medium is aspirated from outside the measuring instrument or is injected into the test compartment under an overpressure.

17. The measuring instrument of claim 14, wherein:

the gaseous medium has a predefined moisture content.

18. The measuring instrument of claim 1, further comprising:

a device for calibrating the weighing device.

19. The measuring instrument of claim 18, wherein:

the calibration device comprises one or more calibration weights, and a center of mass of the one or more calibration weights lies on an axis that is oriented in the direction of the load during a calibration process and passes through a center of gravity of at least one of: the sample receiver and of the sample.

20. A method for determining the moisture content of a sample by measuring a weight loss during a test having a predetermined duration and with a defined temperature profile, using the measuring instrument of claim 1, the method comprising the steps of:

conditioning the test compartment to a prescribed temperature using at least one of the radiation sources;

placing the sample in the conditioned test compartment;

producing a measurement result for the sample weight by at least one of: determining the sample weight at predetermined time intervals and determining the sample weight loss continuously over the test duration; and at least one of: evaluating the measurement result and transmitting the measurement result to an indicating unit.

21. A method for determining a moisture affinity in a sample by measuring a weight increase during a test having a predetermined duration and with a defined temperature profile, using the measuring instrument of claim 1, the method comprising the steps of:

placing the sample in the test compartment;

conditioning the sample in the test compartment to a predetermined moisture content;

setting the test compartment to a prescribed temperature using at least one of the radiation sources;

injecting a gaseous medium with a known moisture content into the test compartment at a predefined volume flow rate and a predefined temperature profile at least over the duration of the test period;

producing a measurement result by at least one of: determining the sample weight at predetermined measurement intervals and determining the weight gain continuously over the test duration; and at least one of: evaluating the measurement result and transmitting the measurement result to an indicator unit.

22. A method for correcting an error in the measurement result determined in the method of claim 20 or claim 21 due to buoyancy, comprising the steps of:

placing a reference object into the test compartment;

determining a base weight value of the reference object;

determining correction weight values for the reference object by at least one of: measuring a weight value in predetermined measurement intervals and measuring the weight change continuously over the test duration;

calculating, by subtracting the base weight value from the correction weight values, at least one of: a set of correction values and a correction profile over the test duration;

storing in a memory module the calculated correction values and/or the correction profile;

removing the reference object from the test compartment; and performing the sample measurement, taking into account the calculated correction values.

* * * * *